(12) United States Patent
Robinson et al.

(10) Patent No.: US 12,329,614 B2
(45) Date of Patent: Jun. 17, 2025

(54) TEARABLE DRESSING STRUCTURE

(71) Applicant: Solventum Intellectual Properties Company, Maplewood, MN (US)

(72) Inventors: Timothy Mark Robinson, Shillingstone (GB); Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 326 days.

(21) Appl. No.: 17/420,983

(22) PCT Filed: Jan. 7, 2020

(86) PCT No.: PCT/US2020/012560
§ 371 (c)(1),
(2) Date: Jul. 6, 2021

(87) PCT Pub. No.: WO2020/159675
PCT Pub. Date: Aug. 6, 2020

(65) Prior Publication Data
US 2022/0096730 A1   Mar. 31, 2022

Related U.S. Application Data

(60) Provisional application No. 62/797,632, filed on Jan. 28, 2019.

(51) Int. Cl.
*A61F 13/05* (2024.01)
*A61F 13/00* (2024.01)
(Continued)

(52) U.S. Cl.
CPC .......... *A61F 13/05* (2024.01); *A61F 13/0206* (2013.01); *A61L 15/26* (2013.01);
(Continued)

(58) Field of Classification Search
CPC ............ A61F 13/00068; A61F 13/0206; A61F 13/0216; A61F 2013/00357; A61M 1/915
See application file for complete search history.

(56) References Cited

U.S. PATENT DOCUMENTS 1,355,846 A   10/1920   Rannells
2,547,758 A   4/1951   Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Jessica Arble
*Assistant Examiner* — Nhu Q. Tran

(57) ABSTRACT

A dressing or wound filler comprising a laminate structure of materials. In one example embodiment, a dressing may include a first layer comprising a first film, a second layer adjacent to the first layer and comprising a foam, and a third layer comprising a second film. The first layer and the second layer may further include a plurality of perforations or fenestrations. The third layer may include a plurality of raised features. The perforations or fenestrations of the first and second layers may be positioned or aligned with the raised features of the third layer so as to facilitate tearing of the dressing for sizing and application purposes. In some embodiments, the first layer may comprise a polyurethane film, the second layer may comprise a polyurethane foam,
(Continued)

and the third layer may comprise an additional polyurethane film.

18 Claims, 9 Drawing Sheets

(51) Int. Cl.
*A61F 13/0206* (2024.01)
*A61L 15/26* (2006.01)
*A61L 15/42* (2006.01)
*A61M 1/00* (2006.01)

(52) U.S. Cl.
CPC ........... *A61L 15/425* (2013.01); *A61M 1/915* (2021.05); *A61F 2013/00357* (2013.01); *A61M 1/92* (2021.05); *A61M 1/96* (2021.05)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,465,729 A * | 8/1984 | Cancio .................... | B44C 1/10 156/244.11 |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,086,764 A * | 2/1992 | Gilman ............... | A61F 13/0203 602/42 |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,238,762 B1 * | 5/2001 | Friedland .................... | C09J 7/20 428/167 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0167729 A1 * | 7/2008 | Nelson .................. | A61F 2/0063 623/23.72 |
| 2009/0227969 A1 * | 9/2009 | Jaeb .................. | A61F 13/00068 604/313 |
| 2011/0224631 A1 * | 9/2011 | Simmons .......... | A61F 13/00995 604/319 |
| 2014/0163491 A1 | 6/2014 | Schuessler et al. | |
| 2015/0080788 A1 | 3/2015 | Blott et al. | |

(56) References Cited

U.S. PATENT DOCUMENTS

| | | | | |
|---|---|---|---|---|
| 2016/0023430 | A1* | 1/2016 | Calkins | B32B 37/12 428/317.1 |
| 2018/0296394 | A1* | 10/2018 | Barberio | A61F 13/00029 |
| 2018/0353662 | A1 | 12/2018 | Locke et al. | |
| 2020/0170842 | A1* | 6/2020 | Locke | A61F 13/00068 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

(56) References Cited

OTHER PUBLICATIONS

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Chinese First Office Action Corresponding to Application No. 2020800094163, mailed Mar. 28, 2022.

\* cited by examiner

TEARABLE DRESSING STRUCTURE

RELATED APPLICATIONS

The present application claims priority to U.S. Provisional Patent Application No. 62/797,632, entitled "Tearable Dressing Structure," filed Jan. 28, 2019, which is incorporated herein by reference for all purposes.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing or wound filler may comprise a laminate structure of materials. Outer layers may comprise film layers, at least one of which may be configured to face a tissue site. For example, the outer layers may comprise a polyurethane film. At least one of the outer layers may have linear perforations or fenestrations formed over the surface. The size and spacing of the perforations or fenestrations may vary. Another of the outer layers may comprise a film having raised features. One or more intermediate spacing layers between the outer layers may comprise a polymer foam, such as a polyurethane foam, which may manifold fluid, provide a compressible filler that can conform to spaces and curves, and can present a barrier to tissue in-growth. An intermediate foam layer may comprise perforations or fenestrations that align with the perforations or fenestrations in the first outer film layer and the raised features of the second outer layer in order to facilitate tearing of the laminate structure.

More generally, in some embodiments, a dressing material may include a first layer comprising a first film of non-porous material having a plurality of openings, a second layer adjacent to the first layer and comprising a manifold having a plurality of slits, and a third layer adjacent to the second layer and comprising a second film of non-porous material having raised features. At least some of the plurality of openings, some of the plurality of slits, and some of the raised features may be aligned to define a tear line. In some embodiments, the first layer may comprise a polyurethane film, the second layer may comprise a polyurethane foam, and the third layer may comprise a polyurethane film.

In other example embodiments, a dressing for treating a tissue site with negative pressure may comprise a foam layer comprising a first plurality of fenestrations, a first film comprising a second plurality of fenestrations, and a second film comprising a plurality of raised features. The first film may be positioned adjacent the first side of the foam layer, and the second film may be positioned adjacent the second side of the foam layer. In some embodiments, the first plurality of fenestrations and the second plurality of fenestrations may be aligned.

In still further example embodiments, a method of manufacturing a dressing material may include laminating a first film to a first side of a foam layer, creating a plurality of fenestrations through the first film and the foam layer, and laminating a second film comprising a plurality of raised features to a second side of the foam layer. In some embodiments, at least a portion of the plurality of raised features of the second film are aligned with at least a portion of the plurality of fenestrations. In some embodiments, creating the plurality of fenestrations may include forming the fenestrations in parallel rows and columns. In some additional embodiments, creating the plurality of fenestrations may include forming fenestrations in a pattern having geometric shapes.

In yet further example embodiments, a system for treating a tissue site may include a wound filler, a plurality of sealing strips, and an interface. The wound filler may include a first layer comprising a first film of non-porous material, a second layer adjacent to the first layer and comprising a foam, a third layer adjacent to the second layer and comprising a second film of non-porous material having raised features, and a plurality of fenestrations extending through the first layer and the second layer. The plurality of sealing strips may be adapted to be positioned over a perimeter of the third layer opposite the second layer. The interface may be adapted to be coupled to the wound filler. The system may further include a negative-pressure source adapted to be fluidly connected to the wound filler through the interface.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
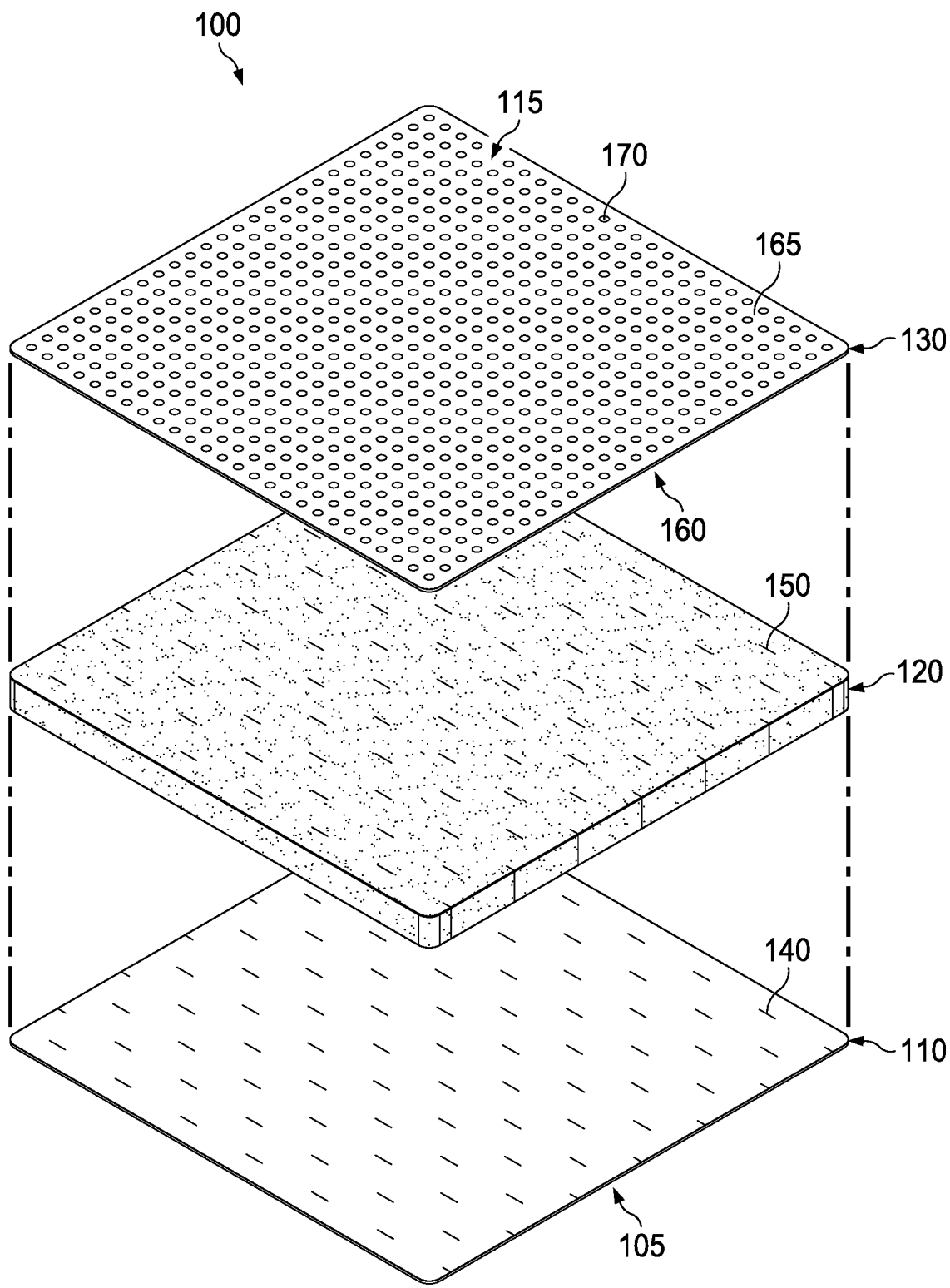
FIG. 1 is an assembly view of an example of a tissue interface, illustrating details that may be associated with some example embodiments.

FIG. 1 is an assembly view of an example of a tissue interface 100 for applying to a tissue site. The tissue interface 100 can be generally adapted to partially or fully contact a tissue site. If the tissue site is a wound, for example, the tissue interface 100 may partially or completely fill the wound, or may be placed over the wound. The tissue interface 100 may have a first side 105 and a second side 115. The tissue interface 100 may include a first layer 110, a second layer 120, and a third layer 130. In some embodiments, the first layer 110, the second layer 120, and the third layer 130 may be stacked so that the second layer 120 is adjacent to and in contact with the first layer 110 and the third layer 130. The second layer 120 may also be laminated or bonded to the first layer 110, the third layer 130, or both in some embodiments. In some embodiments, the first layer 110 may be adapted to be placed against a tissue site, such as a wound and surrounding periwound area.

The tissue interface 100 may take many forms, and may have many sizes, shapes, or thicknesses, depending on a variety of factors, such as the type of treatment being implemented or the nature and size of a tissue site. While the tissue interface 100 is shown in FIG. 1 overall to have substantially a square shape, the tissue interface 100 and included layers may be any number of different shapes, based on the particular anatomical needs of a tissue site. For example, the tissue interface 100 and included layers may have a square, rectangular, oval, circular, hexagonal, or other shape. For example, the size and shape of the tissue interface 100 may be adapted to the contours of deep and irregular shaped tissue sites. Any or all of the surfaces of the tissue interface 100 may have an uneven, coarse, or jagged profile.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue.

The first layer 110 may comprise or consist essentially of a means for controlling or managing fluid flow. In some embodiments, the first layer 110 may comprise or consist essentially of a liquid-impermeable material. For example, the first layer 110 may comprise or consist essentially of a non-porous polymer film. The first layer 110 may also have a smooth or matte surface texture in some embodiments. In some embodiments, variations in surface height may be limited to acceptable tolerances. For example, the surface of the first layer 110 may have a substantially flat surface, with height variations limited to 0.2 millimeters over a centimeter.

In some embodiments, the first layer 110 may comprise or consist essentially of a polymeric film. In some embodiments, the first layer 110 may comprise or consist essentially of a hydrophilic polymeric film, while in additional or alternative embodiments, the first layer 110 may comprise or consist essentially of a hydrophobic polymeric film. In some embodiments, the first layer 110 may comprise or consist essentially of a polyurethane film. For example, the first layer 110 may comprise an Inspire 2301 or Inspire 2327 polyurethane film, commercially available from Expopack Advanced Coatings, Wrexham, United Kingdom. In some applications, the first layer 110 may have a high moisture-vapor transmission rate (MVTR). For example, the MVTR may be at least 250 grams per square meter per twenty-four hours in some embodiments, measured using an upright cup technique according to ASTM E96/E96M Upright Cup Method at 38° C. and 10% relative humidity (RH). For example, the first layer 110 may comprise INSPIRE 2301 having an MVTR (upright cup technique) of 2600 g/m$^2$/24 hours and a thickness of about 30 microns. Other suitable polymeric films may include polyethylenes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. Films may be clear, colored, or printed. In some embodiments where the first layer 110 may comprise a polyethylene film, more polar films suitable for laminating to a polyethylene film include polyamide, copolyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations. In some embodiments, the hydrophobicity of the first layer 110 may be further enhanced with a hydrophobic coating of other materials, such as silicones and fluorocarbons, either as coated from a liquid or plasma coated.

In some embodiments, the first layer 110 may comprise an adhesive coating, which may be exposed on the first side 105 of the tissue interface 100. In some embodiments, the adhesive coating may comprise a low-tack medically-acceptable adhesive. For example, the adhesive coating may comprise a silicone gel, a polyurethane gel, or a low-tack acrylic adhesive. In some instances, the adhesive coating may have a low coat weight, such as between 25 grams per square meter and 100 grams per square meter, which may maintain the high MVTR of the first layer 110. The thickness of the adhesive coating may be tailored to balance the need to provide a good seal with the tissue site, while also maintaining a high MVTR. The adhesive coating may also be pattern coated on the first layer 110 in order to maintain the high MVTR of the first layer 110. The adhesive coating may assist with keeping the tissue interface 100 in place during application, which may be helpful to the user while finalizing the placement of the tissue interface 100 and sealing the tissue interface 100 to the tissue site.

The first layer 110 may also be suitable for laminating, adhering, or welding to other layers, including the second layer 120. For example, the first layer 110 may be flame laminated to the second layer 120. The first layer 110 may also be secured to the second layer 120 using a non-woven or mesh hot-melt material. For example, a nonwoven or mesh hot-melt material may be applied to the surface of the second layer 120, with the first layer 110 being applied over the hot-melt material. Heat and pressure may then be applied to melt the nonwoven or mesh hot-melt material in order to bind the first layer 110 to the second layer 120. In some embodiments, the first layer 110 may be adapted for welding to the second layer 120, which may be a foam, using heat, radio-frequency (RF) welding, or other methods to generate heat such as ultrasonic welding. RF welding may be particularly suitable for more polar materials, such as polyurethane, polyamides, polyesters, and acrylates. Sacrificial polar interfaces may be used to facilitate RF welding of less polar film materials such as polyethylene. In some additional or alternative embodiments, the first layer 110 may comprise a film having an adhesive coating on a surface for adhering to the second layer 120.

As illustrated in the example of FIG. 1, the first layer 110 may have one or more openings 140, which may be distributed uniformly across the first layer 110. The openings 140 may be bi-directional and pressure-responsive. For example, each of the openings 140 generally may comprise or consist essentially of an elastic passage that is normally unstrained to substantially reduce liquid flow, and can expand or open in response to a pressure gradient. The openings 140 may be in the form of fenestrations or perforations. In some embodiments, the openings 140 may comprise or consist essentially of fenestrations in the first layer 110. Fenestrations may be formed by removing material from the first layer 110, and may result in edges that are not deformed. In some alternative or additional embodiments, the openings 140 may comprise or consist essentially of perforations in the first layer 110. Perforations may be formed by removing material from the first layer 110. For example, perforations may be formed by cutting through the first layer 110. The amount of material removed and the resulting dimensions of the perforations may be an order of magnitude more than fenestrations, which may result in edges that are deformed. Additionally, in some embodiments, perforations may be formed by mechanical slitting then controlled uni- and/or bi-axial stretching of the film material of the first layer 110.

For example, some embodiments of the openings 140 may comprise or consist essentially of one or more slits, slots, or combinations of slits and slots in the first layer 110. In some examples, the openings 140 may comprise or consist of linear slots having a length less than 6 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, ultrasonics, or other heat means, for example. The linear slits or slots may be spaced apart by about 2 to 4 millimeters along their length and from side-to-side.

The second layer 120 generally comprises or consists essentially of a manifold or a manifold layer, which provides a means for collecting or distributing fluid across the tissue interface 100 under pressure. For example, the second layer 120 may be adapted to receive negative pressure from a source and distribute negative pressure through multiple apertures across the tissue interface 100, which may have the effect of collecting fluid from across a tissue site and drawing the fluid toward the source.

In some illustrative embodiments, the second layer 120 may comprise a plurality of pathways, which can be interconnected to improve distribution or collection of fluids. In some embodiments, the second layer 120 may comprise or consist essentially of a porous material having interconnected fluid pathways. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways.

In some embodiments, the second layer 120 may comprise or consist essentially of a polymeric foam, such as a polyurethane foam. For example, the second layer 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of second layer 120 may also vary according to needs of a prescribed therapy. The 25% compression load deflection of the second layer 120 may be at least 0.35 pounds per square inch, and the 65% compression load deflection may be at least 0.43 pounds per square inch. In some embodiments, the tensile strength of the second layer 120 may be at least 10 pounds per square inch. The second layer 120 may have a tear strength of at least 2.5 pounds per inch. In some embodiments, the second layer 120 may be foam comprised of polyols such as polyester or polyether, isocyanate such as toluene diisocyanate, and polymerization modifiers such as amines and tin compounds. In some examples, the second layer 120 may be reticulated polyurethane foam such as found in GRANUFOAM™ dressing or V.A.C. VERAFLO™ dressing, both available from Kinetic Concepts, Inc. of San Antonio, Texas.

In some additional or alternative embodiments, the second layer 120 may be hydrophilic and may also wick fluid away from a tissue site, while being able to continue to distribute a negative pressure to the tissue site. The wicking properties of the second layer 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

The thickness of the second layer 120 may also vary according to needs of a prescribed therapy. For example, the thickness of the second layer 120 may be decreased to reduce tension on peripheral tissue. The thickness of the second layer 120 can also affect the conformability of the second layer 120 and the tissue interface 100. In some embodiments, a thickness in a range of about 4 millimeters to 12 millimeters may be suitable, and in some more specific embodiments, the second layer 120 may have a thickness between 6 millimeters and 10 millimeters. In some embodiments, the second layer 120 may be partially or completely opaque, or otherwise be such that the second layer 120 may block at least a portion of light passage.

As illustrated in the example of FIG. 1, the second layer 120 may include a plurality of slits 150, which may be distributed uniformly across the second layer 120. The slits 150 may be in the form of fenestrations or tears through a portion or the entire thickness of the second layer 120. For example, the second layer 120 may comprise a reticulated polyurethane foam having slits 150 in the form of finely-cut linear fenestrations. In some embodiments, the slits 150 may be arranged in parallel rows, which may be offset from each other in some instances. In some additional embodiments, the slits 150 may be arranged in both parallel and perpendicular rows. The slits 150 may correspond to or be aligned with at least some of the openings 140 in the first layer 110. In some examples, the slits 150 may comprise or consist of linear fenestrations having a length of between 1 millimeter and 6 millimeters, and a width less than 1 millimeter. In some embodiments, a length of about 3 millimeters may be particularly suitable for many applications, and a tolerance of about 0.1 millimeters may also be acceptable. The slits 150 may be spaced apart by about 2 millimeters to 4 millimeters along their length and from side-to-side between the adjacent rows of the slits 150, in some examples.

The slits 150 of the second layer 120 may be formed using a variety of mechanisms. For example, the slits 150 may be formed using a knife or other blade to make fine cuts in the second layer 120. In such instances, the slits 150 may have a virtually negligible width, as little to none of the material of the second layer 120 is removed during the cutting with the knife or other form of blade. In other embodiments, the slits 150 may be formed using laser cutting, which may result in the slits 150 having a width of between 0.3 mm and 0.5 mm in some instances. Using laser cutting may evaporate the material of the second layer 120 in order to form the slit 150, without leaving any appreciable amount of material of the second layer 120 behind. In other embodiments, ultrasonic cutting may be used to form the slits 150 in the second layer 120.

The third layer 130 may be constructed from a material that can provide a seal between two environments, such as between a therapeutic environment and a local external environment. For example, the third layer 130 may be adapted to provide a sealing layer over the first layer 110 and the second layer 120 of the tissue interface 100, and the material of the third layer 130 may be capable of maintaining a negative pressure at a tissue site. The third layer 130 may generally comprise or consist essentially of a film layer formed from a soft, flexible material. In some embodiments, the third layer 130 may be constructed from a thin film that is highly-breathable. For example, the third layer 130 may comprise an elastomeric film that can provide a seal for maintaining a negative pressure at a tissue site. The third layer 130 may have a high moisture-vapor transmission rate (MVTR) in some embodiments. In some example embodiments, the third layer 130 may be a polyurethane film that is permeable to water vapor, but impermeable to liquid. For example, the third layer 130 may comprise a film formed from a polyurethane copolymerized with an elastane in order to increase the stretching capability of the third layer 130. In some additional embodiments, the third layer 130 may comprise, for example, a polyethylene, polyester, or copolyester film. In some embodiments, the film of the third layer 130 may have a thickness in the range of 25-50 microns.

The third layer 130 may include a first side 160 and a second side 165. In some embodiments, the first side 160 may comprise an adhesive coating for adhering to an upper-facing side of the second layer 120. For example, the adhesive coating may be a medically-acceptable acrylic adhesive. The third layer 130 may also include a plurality of raised features 170. For example, the raised features 170 may be formed as a plurality of embossed protrusions on the second side 165 of the third layer 130. In some embodiments, the raised features 170 may be in the form of a plurality of raised features arranged in a series of parallel rows. For example, the raised features 170 may comprise a plurality of textured, raised hemispheres, and may have a diameter in a range between 0.5 millimeters and 5 millimeters. Other shapes and sizes for the raised features 170 may also be applicable. The raised features 170 may be spaced apart between about 1 millimeter and 5 millimeters within rows, and may be spaced side-to-side by about 1 millimeter. The raised features 170 may further enhance the breathability of the film of the third layer 130.

In some additional or alternative embodiments, the third layer 130 may comprise a material that has raised features 170 as well as a plurality of perforations. For example, the third layer 130 may be a Transpore™ surgical tape, supplied by 3M of Maplewood, Minnesota. In such embodiments, an additional sealing layer may be included over the third layer 130 on the second side 115 of the tissue interface 100 in order to provide a sealed environment around the other layers of the tissue interface 100 for maintaining a negative pressure.

The first layer 110, the second layer 120, the third layer 130, or various combinations may be assembled before application or in situ. In some embodiments, the tissue interface 100 may be manufactured and/or provided in its assembled, stacked configuration, for example with the first layer 110 laminated to the second layer 120, and the third layer 130 also laminated to the second layer 120 opposite the first layer 110. In some instances, the first layer 110 may be laminated to the second layer 120, and then perforations or fenestrations may be made through both of the laminated layers to form the openings 140 of the first layer 110 and the slits 150 of the second layer 120. In some alternative embodiments, the openings 140 may be first made in the first layer 110, and the slits 150 may be separately made in the second layer 120, before the first layer 110 and the second layer 120 are laminated together in a stacked configuration.

In some embodiments, the layers of the tissue interface 100 may be coextensive. For example, the first layer 110 may be flush with the edges of the second layer 120 and with the edges of the third layer 130, exposing the edges of the second layer 120 between the first layer 110 and the third layer 130, as illustrated in the embodiment of FIG. 1. In some alternative embodiments, one or more of the layers of the tissue interface 100 may not be coextensive with each other. The laminated stack of tissue interface layers may allow the tissue interface 100 to be sized by simultaneously tearing through the stacked layers of the tissue interface 100.

Figure 2:
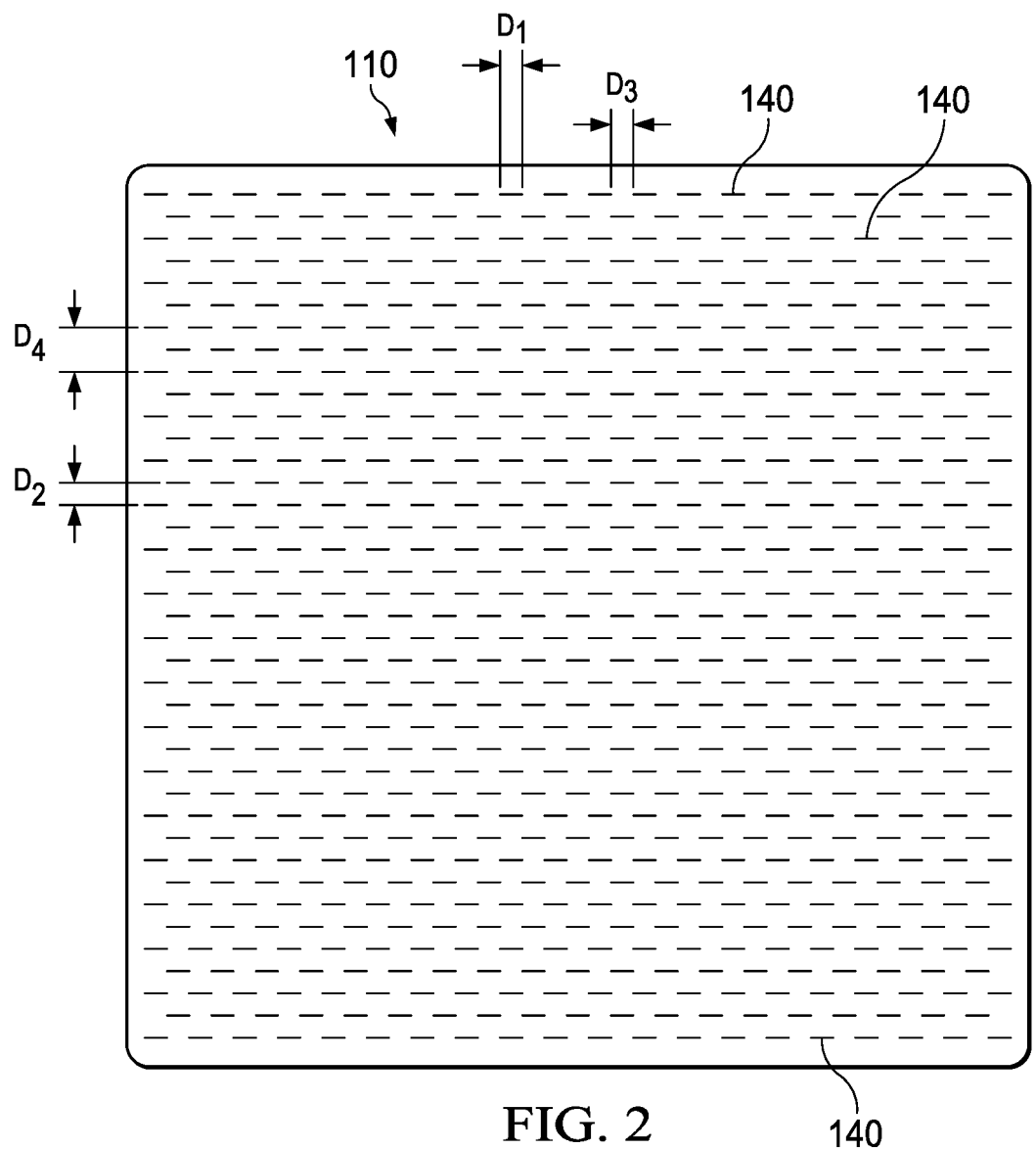
FIG. 2 is a schematic view of an example configuration of fluid openings in a layer that may be associated with some embodiments of the tissue interface of FIG. 1.

FIG. 2 is a schematic view of an example of the first layer 110, illustrating additional details that may be associated with some embodiments. As illustrated in the example of FIG. 2, the openings 140 may each consist essentially of one or more linear slots having a length $D_1$, which may be about 3 millimeters. FIG. 2 additionally illustrates an example of a uniform distribution pattern of the openings 140. In FIG. 2, the openings 140 are substantially coextensive with the first layer 110 and are distributed across the first layer 110 in a grid of parallel rows and columns, in which the slots are also mutually parallel to each other. In some embodiments, the rows may be spaced by a distance $D_2$, which may be about 3 millimeters on center, and the openings 140 within each of the rows may be spaced by a distance $D_3$, which may be about 3 millimeters on center as illustrated in the example of FIG. 2. The openings 140 in adjacent rows may be aligned or offset. For example, adjacent rows may be offset, as illustrated in FIG. 2, so that the openings 140 are aligned in alternating rows and separated by a distance $D_4$, which may be about 6 millimeters. The spacing of the openings 140 may vary in some embodiments to increase the density of the openings 140 according to therapeutic requirements. Although not shown in FIG. 2, the openings 140 of the first layer 110 may be arranged in a variety of different patterns. For example, in some alternative embodiments, the openings 140 may be arranged in a grid with perpendicular rows. In some further embodiments, the openings 140 may be arranged in geometric patterns or shapes to facilitate tearing of the first layer 110 (and the other layers of the tissue interface 100) in squares, circles, spirals, or other geometric shapes. For example, the slits 150 of the second layer 120 may be arranged in rows or geometric patterns corresponding to the arrangement of the openings 140 of the first layer 110.

Figure 3:
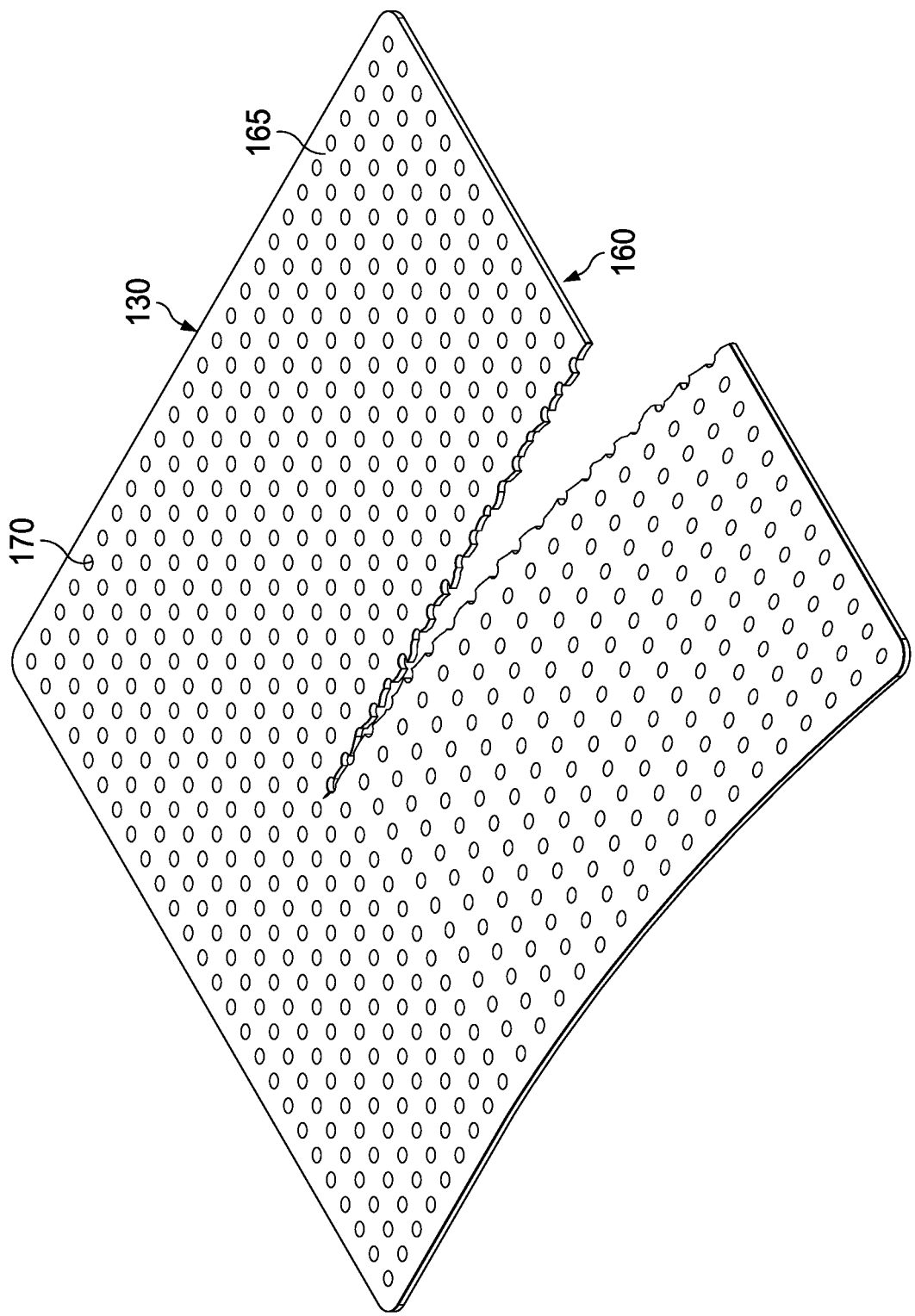
FIG. 3 is a schematic view of an example configuration of raised features in another layer that may be associated with some embodiments of the tissue interface of FIG. 1.

FIG. 3 is a schematic view of an example of the third layer 130, illustrating additional details that may be associated with some embodiments. The first side 160 of the third layer 130 may have an adhesive coating in some examples. As illustrated in FIG. 3, the raised features 170 may be arranged in a uniform distribution pattern, and the raised features 170 may be substantially coextensive with the third layer 130. Similarly to the openings 140 of the first layer 110 of FIG. 2, the raised features 170 may be arranged across the third layer 130 in a grid of parallel rows and columns. The rows of raised features 170 may be spaced corresponding to the spacing of the rows of openings 140 of the first layer 110, to generally align the rows of raised features 170 and the rows of openings 140 of the first layer 110, which may facilitate tearing through the tissue interface 100. In some embodiments, the raised features 170, along with the openings 140 of the first layer 110 and the slits 150 of the second layer 120, may be arranged in both parallel and perpendicular rows, in order to facilitate tearing and sizing of the tissue interface 100 in multiple directions. The raised features 170 may also be arranged in geometric patterns or shapes, such as squares, circles, or spirals, so that the raised features 170 may align with the openings 140 of the first layer 110 and slits 150 of the second layer 120 that are arranged in such a geometric pattern, in order to facilitate tearing and sizing the tissue interface 100 in such shapes and patterns.

Figure 4:
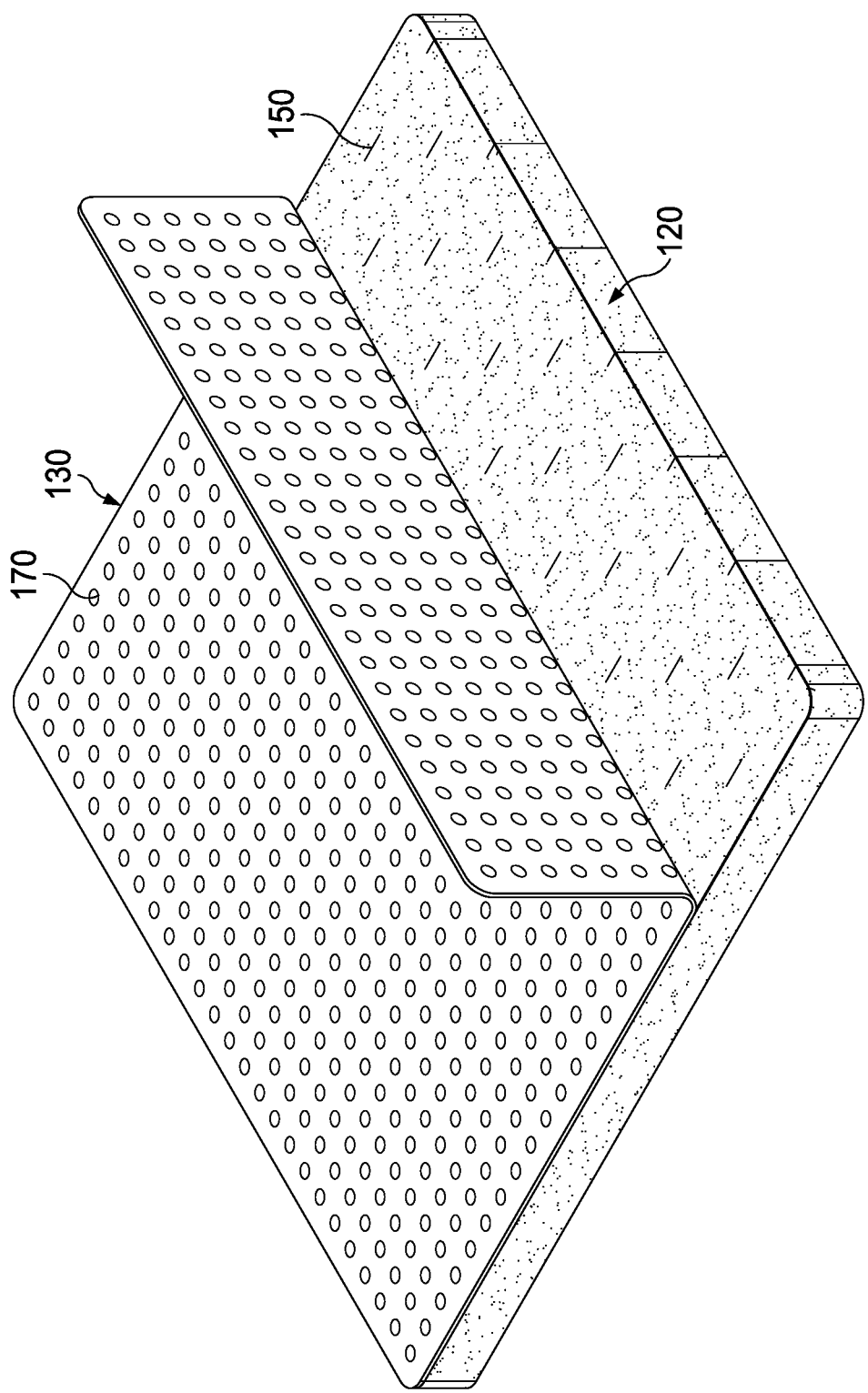
FIG. 4 is a schematic view of a portion of the example layer of FIG. 3 overlaid on a portion of another layer that may be associated with some embodiments of the tissue interface of FIG. 1, illustrating details that may be associated with a relaxed state of the layers.

FIG. 4 is a schematic view of an example of the second layer 120 and the third layer 130, according to some embodiments. In the representative illustration of FIG. 4, the third layer 130 has been partially removed to expose a portion of the second layer 120, with the remaining section of the third layer 130 being adhered or laminated to the second layer 120. FIG. 4 illustrates portions of the second layer 120 having slits 150 and the third layer 130 having raised features 170, where the second layer 120 and the third layer 130 are in a relaxed, or non-stretched state. In the pictured relaxed state, the slits 150 may be difficult to observe due to the nature of the foam material of the second layer 120. At least some of the rows of the raised features 170 of the third layer 130 may be aligned with or overlaid on rows of slits 150 of the second layer 120 to facilitate even and aligned tearing of the second layer 120 and the third layer 130.

Figure 5:
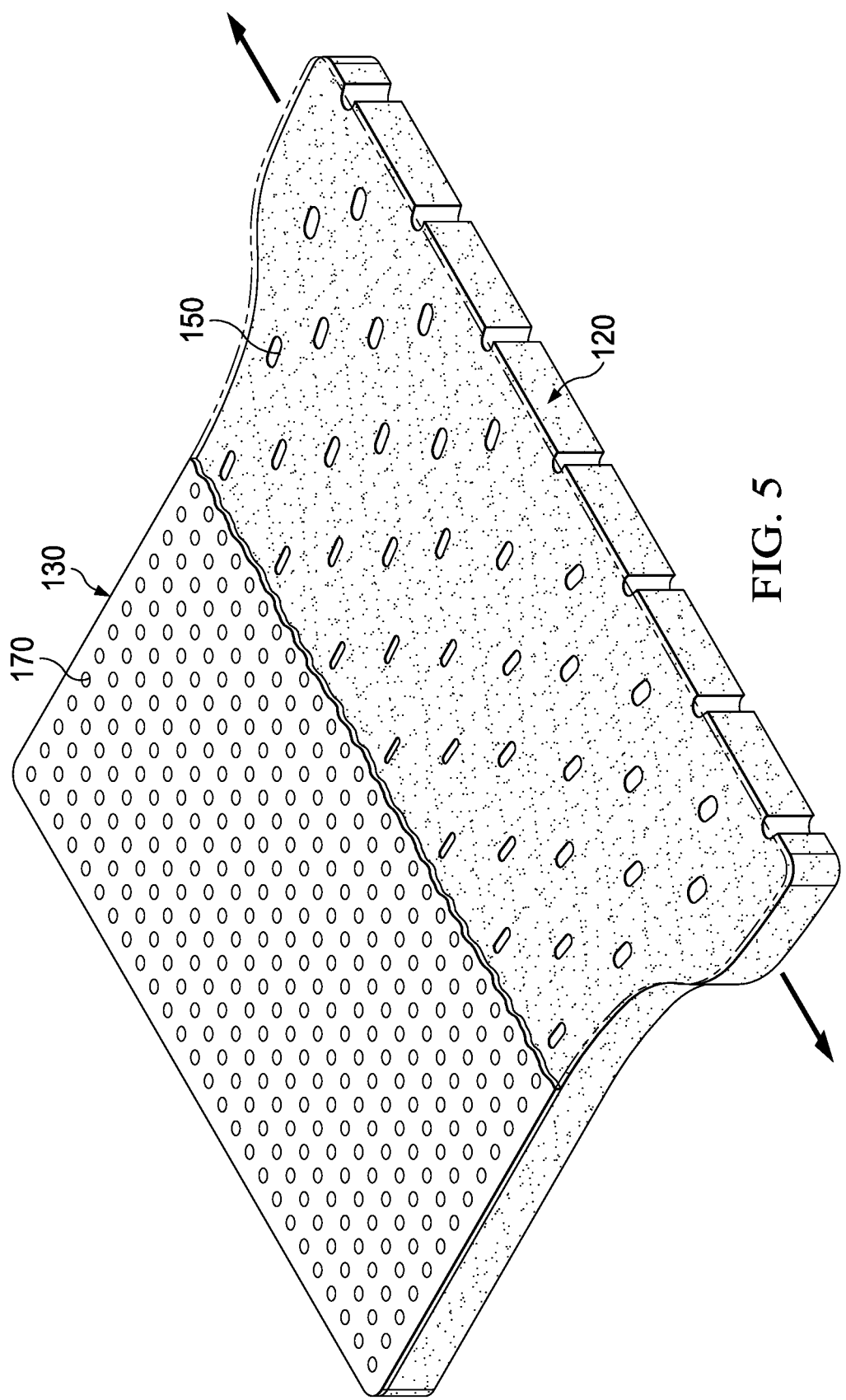
FIG. 5 is a schematic view of the overlaid layers shown in FIG. 4, illustrating details that may be associated with a stretched state of the layers.

FIG. 5 is a schematic view of the example portions of the second layer 120 and the third layer 130 of FIG. 4, showing additional details according to some illustrative embodiments. In the representative illustration of FIG. 5, a portion of the third layer 130 has been removed to expose a portion of the second layer 120. Specifically, FIG. 5 illustrates the portion of the second layer 120 in a non-relaxed, or stretched state. As shown in FIG. 5, upon being stretched, the slits 150 of the second layer 120 may become significantly more visible. As such, by at least slightly stretching a portion of the second layer 120, one or more rows of the slits 150 may be readily identifiable, which may assist with determining the appropriate point to tear the second layer 120 for purposes of sizing the tissue interface 100. Such visualization may also allow a row of raised features 170 of the third layer 130 to be aligned with the row of slits 150 along which the tissue interface 100 may be torn. Such alignment of the raised features 170 of the third layer 130 and the row of slits 150 of the second layer 120 may ensure that torn edges of the second layer 120 and the third layer 130, and overall the tissue interface 100, are substantially flush with each other.

Figure 6:
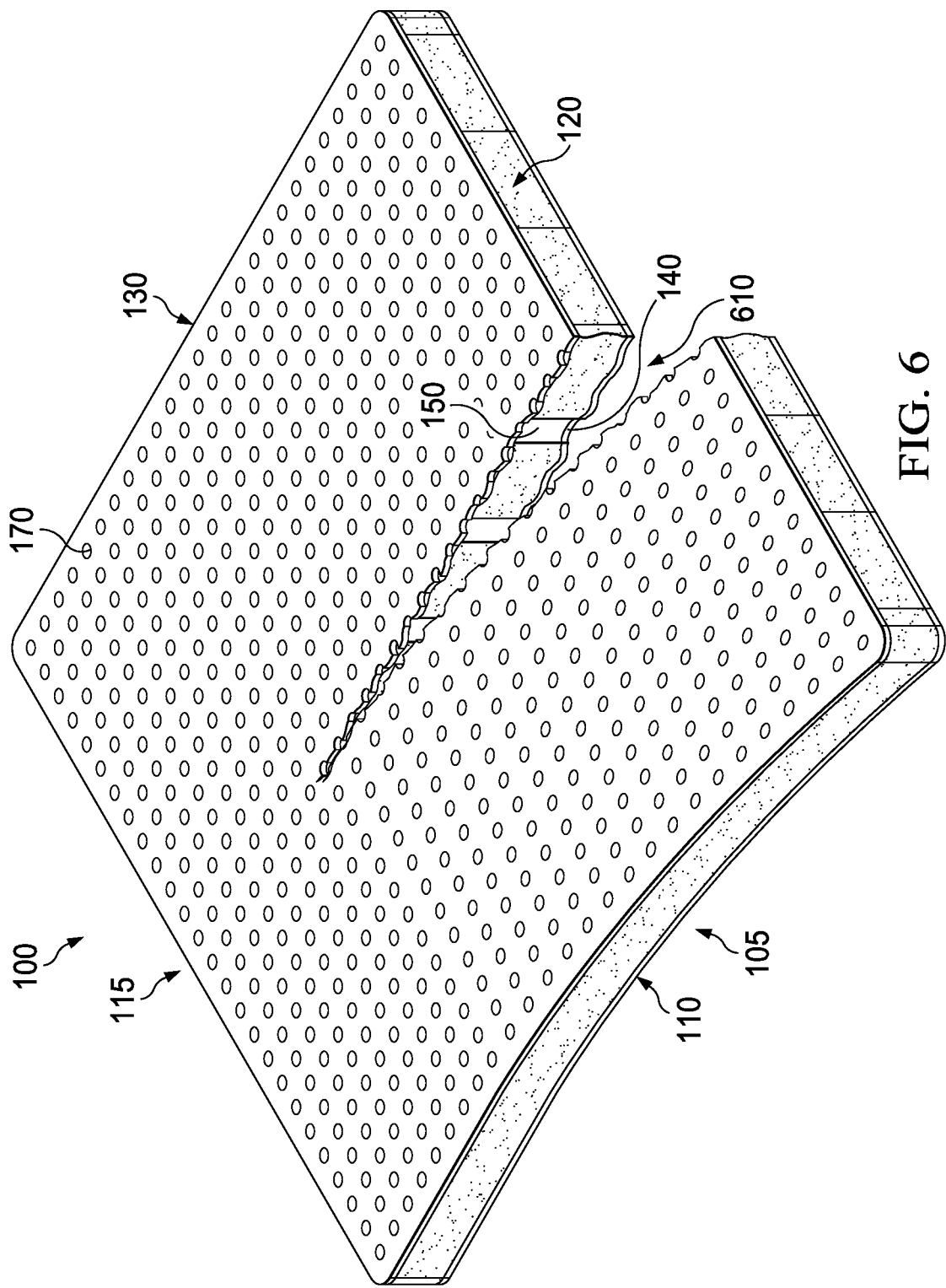
FIG. 6 is a schematic view of overlaid layers associated with some embodiments of the tissue interface of FIG. 1, illustrating details that may be associated with tearing through portions of the overlaid layers.

FIG. 6 is a schematic view of an example portion of a tissue interface 100, showing some details that may be viewed from a top-facing or second side 115 of the tissue interface 100, according to some illustrative embodiments. More specifically, FIG. 6 illustrates how an example of the tissue interface 100 may be sized by tearing through the third layer 130, second layer 120, and underlying first layer 110 along a desired tear line 610 of the tissue interface 100. For example, a tear line 610 may exist where at least a portion of a row of openings 140 of the first layer 110, a portion of a row of slits 150 of the second layer 120, and a portion of a row of raised features 170 of the third layer 130 are aligned. However, the individual openings 140, slits 150, and raised features 170 along the respective rows of openings 140, slits 150, and raised features 170 do not necessarily have to align with each other between the first layer 110, the second layer 120, and the third layer 130. Additionally, not all rows of openings 140, slits 150, and raised features 170 may correspond to a tear line. As illustrated in the example of FIG. 6, portions of the first layer 110, the second layer 120, and the third layer 130 may be torn along the tear line 610, corresponding to a row of the openings 140, a row of the slits 150, and a row of the raised features 170. Through such tearing and separation of the portions of the first layer 110, second layer 120, and third layer 130, the layers of the tissue interface 100 may be sized to a corresponding tissue site.

Figure 7:
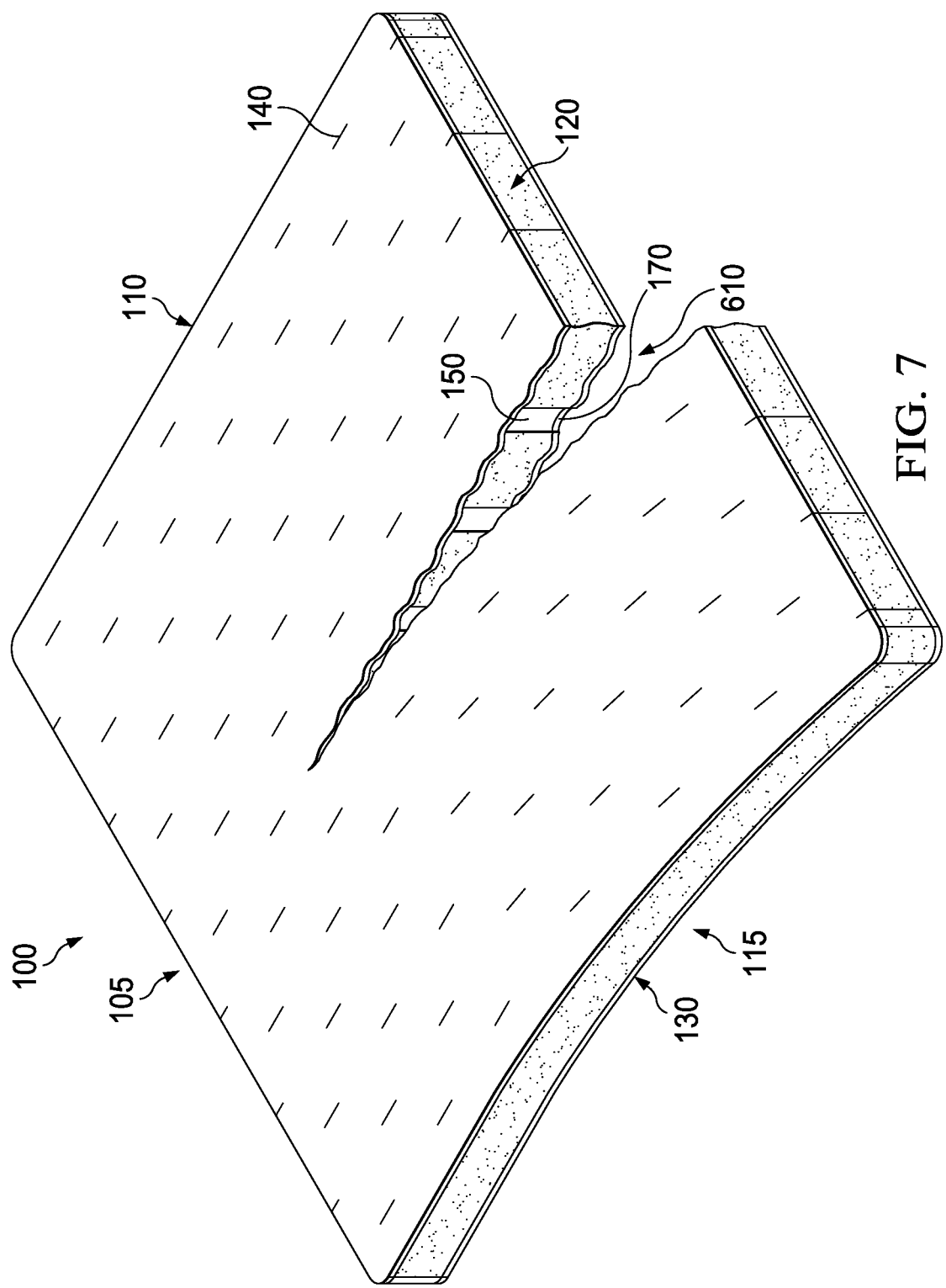
FIG. 7 is another schematic view of overlaid layers associated with some embodiments of the tissue interface of FIG. 1, illustrating details that may be associated with tearing through portions of the overlaid layers.

FIG. 7 is a schematic view of the example portion of the tissue interface 100 of FIG. 6, showing further details that may be viewed from the first side 105 of the tissue interface 100, according to some illustrative embodiments. More specifically, the view of the first side 105 of the tissue interface 100 of FIG. 7 illustrates how the first layer 110 may also be torn along the tear line 610 of the tissue interface 100, which may align with a row of openings 140 of the first layer 110. As collectively shown by FIGS. 6 and 7, the tissue interface 100 may be torn along the tear line 610, which may correspond to and align with a row of openings 140 of the first layer 110, a row of slits 150 of the second layer 120, and a row of raised features 170 of the third layer 130.

Figure 8:
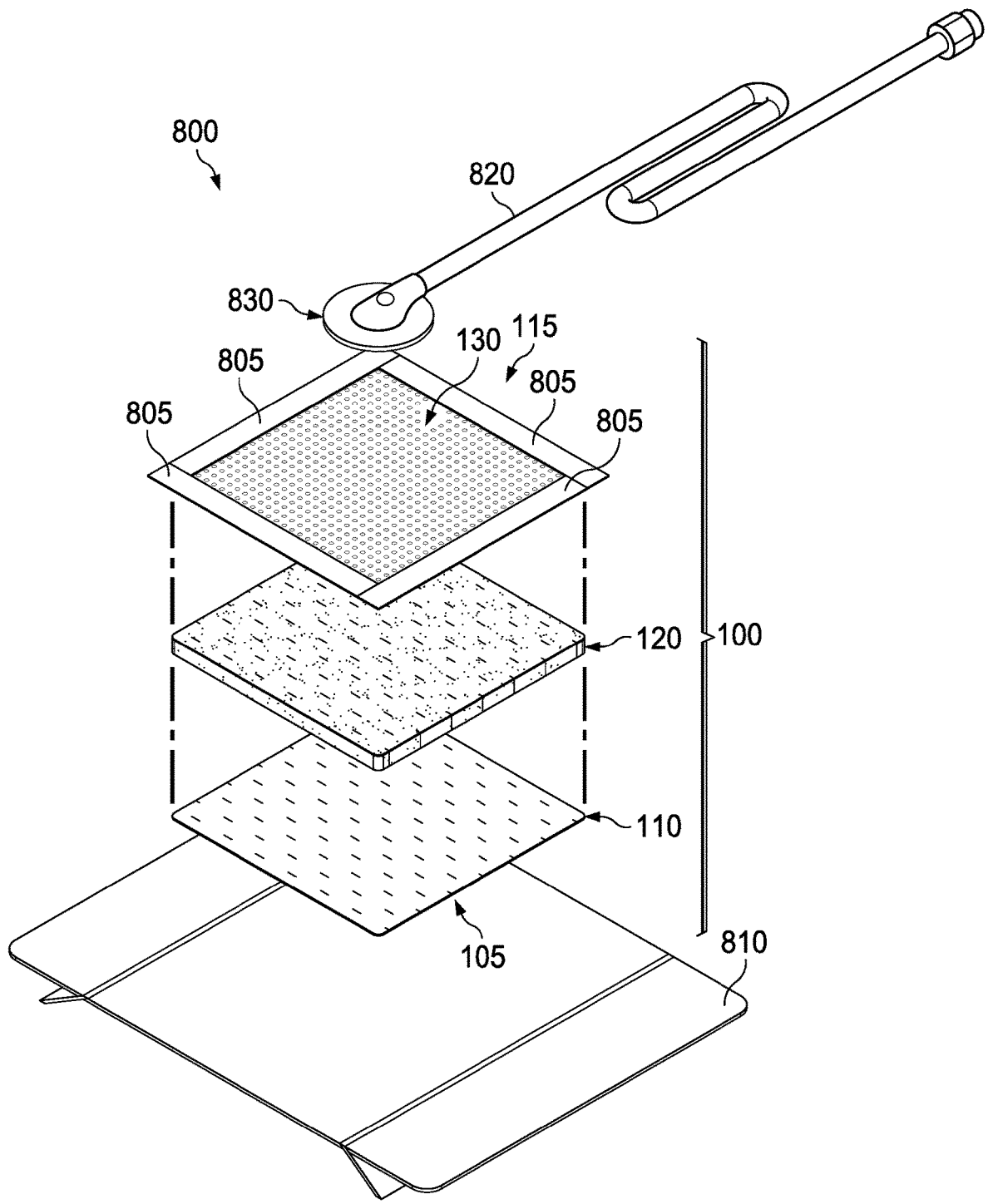
FIG. 8 is an assembly view of an example of a dressing that may incorporate the tissue interface of FIG. 1, according to some illustrative embodiments.

FIG. 8 is an assembly view of a dressing 800 which may incorporate an embodiment of the tissue interface 100 of FIG. 1, according to some illustrative embodiments. For example, the dressing 800 may include the tissue interface 100, along with additional components that may enable or particularly facilitate use of the dressing 800 and associated tissue interface 100 with negative-pressure therapy. As shown in FIG. 8, the dressing 800 may comprise the tissue interface 100, which may include the first layer 110, the second layer 120, and the third layer 130 arranged in a stacked formation.

As shown in FIG. 8, in some embodiments, the dressing 800 may include a plurality of sealing strips 805, which may be positioned around the perimeter of the tissue interface 100 and sealed to an attachment surface, such as epidermis peripheral to a tissue site, to provide an effective seal around the edges of the tissue interface 100. The sealing strips 805 may be applied to a perimeter of the third layer 130. For example, four individual sections of sealing strips 805 may be used to seal the third layer 130 to an epidermis, with each of the four sections of sealing strips 805 being applied to one of the four edges of the third layer 130. In some embodiments, the sealing strips 805 may comprise polymer strips, such as polyurethane strips, having an adhesive, such as an acrylic adhesive, thereon. In some embodiments, the sealing strips 805 may further or alternatively include additional layers, such as a gel layer.

As illustrated in the example of FIG. 8, in some embodiments, the dressing 800 may include a release liner 810 to protect the first side 105 of the tissue interface 100 prior to use. The release liner 810 may also provide stiffness to assist with, for example, deployment of the dressing 800. The release liner 810 may be, for example, a casting paper, a film, or polyethylene. Further, in some embodiments, the release liner 810 may be a polyester material such as polyethylene terephthalate (PET) or similar polar semi-crystalline polymer. The use of a polar semi-crystalline polymer for the release liner 810 may substantially preclude wrinkling or other deformation of the dressing 800. For example, the polar semi-crystalline polymer may be highly orientated and resistant to softening, swelling, or other deformation that may occur when brought into contact with components of the dressing 800 or when subjected to temperature or environmental variations, or sterilization. Further, a release agent may be disposed on a side of the release liner 810 that is configured to contact the first layer 110 on the first side 105 of the tissue interface 100. For example, the release agent may be a silicone coating and may have a release factor suitable to facilitate removal of the release liner 810 by hand and without damaging or deforming the dressing 800. In some embodiments, the release agent may be a fluorocarbon or a fluorosilicone, for example. In other embodiments, the release liner 810 may be uncoated or otherwise used without a release agent.

FIG. 8 also illustrates one example of a fluid conductor 820 and a dressing interface 830. As shown in the example of FIG. 8, the fluid conductor 820 may be a flexible tube, which can be fluidly coupled on one end to the dressing interface 830. The dressing interface 830 may be an elbow connector, as shown in the example of FIG. 8, which can be placed over an aperture on the upper, or second side 115 of the tissue interface 100 to provide a fluid path between the fluid conductor 820 and the tissue interface 100. For example, such an aperture may be a centrally-positioned aperture in the third layer 130 that is cut or torn by a user. In some embodiments, the fluid conductor 820 may also include a fluid delivery conduit for use with instillation therapy. Further, in some embodiments, the dressing interface 830 may include multiple fluid conduits, such as a conduit for communicating negative pressure and a fluid delivery conduit. For example, the dressing interface 830 may be a V.A.C. VERAT.R.A.C.™ Pad or a SENSA-T.R.A.C.™ Pad, available from KCI of San Antonio, Texas.

Individual components of the tissue interface 100, and more generally the dressing 800, may be bonded or otherwise secured to one another with a solvent or non-solvent adhesive, or with thermal welding, for example, without adversely affecting fluid management. In some embodiments of the tissue interface 100, one or more components may additionally be treated with an antimicrobial agent. For example, the first layer 110, the second layer 120, and/or the third layer 130 may be coated with an antimicrobial agent. In some examples, the fluid conductor 820, the dressing interface 830, or other portion of the dressing 800 may additionally or alternatively be treated with one or more antimicrobial agents. Suitable agents may include, for example, metallic silver, PHMB, iodine or its complexes and mixes such as povidone iodine, copper metal compounds, chlorhexidine, or some combination of these materials. Additionally or alternatively, one or more of the components of the tissue interface 100 may be coated with a mixture that may include citric acid and collagen, which can reduce bio-films and infections.

In additional embodiments, the dressing 800 may be provided with different combinations of the individual layers and components. For example, the tissue interface 100 may be provided as a standalone product for applying to a tissue site. In some further embodiments, individual layers of the dressing 800 may be omitted. More specifically, in some alternative embodiments, one or more layers of the tissue interface 100 may be omitted or substituted for another layer. For example, in some embodiments, the tissue interface 100 may comprise only the first layer 110 and the second layer 120, with the film of the third layer 130 being omitted. In such embodiments, the tissue interface 100, including the first layer 110 and the second layer 120, may be applied to a tissue site, with an additional sealing layer, such as a cover, being applied over the first layer 110 and second layer 120. In other embodiments, the tissue interface 100 may comprise a foam layer sandwiched between two fenestrated film layers. For example, such an embodiment may comprise the first layer 110 having openings 140, the second layer 120 comprising a polymeric foam and having slits 150, and an additional film layer having openings, such as a layer identical to the first layer 110. In such embodiments, the foam layer and the two surrounding film layers may be stacked and laminated to each other, and then subsequently, fenestrations may be formed through all three of the layers at once using any of the cutting techniques previously mentioned, such as laser cutting, ultrasonics, or cutting using a knife or other blade.

In use, the tissue interface 100 may be sized to a specific region or anatomical area through cutting or tearing. The release liner 810 (if included) may be removed from the first side 105 of the tissue interface 100. The tissue interface 100 may then be torn by hand, with or without the use of any tools or instruments, along one or more tear lines that may be formed through the multiple layers of the tissue interface 100. For example, the tear line may correspond to or be aligned with a row of the openings 140 of the first layer 110, a row of slits 150 of the second layer 120, and a row of raised features 170 of the third layer 130, so as to form a complete tear or cut through the layers of the tissue interface 100. The tear line may be made through the layers of the tissue interface 100 according to any pattern or shape, such as circles, squares, etc., formed by the openings 140, slits 150, and raised features 170. Thus, once sized, the tissue interface 100 may have a surface area of a circle, square, rectangle, etc. The tissue interface 100 may be torn or cut to an appropriate size without the individual layers, such as the first layer 110, second layer 120, and third layer 130, becoming separated from each other or falling apart.

Once the tissue interface 100 is sized and/or shaped to the area of the tissue site, the tissue interface 100 may be placed within, over, on, or otherwise proximate to the tissue site, particularly a surface tissue site and adjacent epidermis. The first layer 110 may be interposed between the second layer 120 and the tissue site. For example, the first layer 110 may be positioned over a surface wound (including edges of the wound) and undamaged epidermis to prevent direct contact between the second layer 120 and the epidermis. Treatment of a surface wound or placement of the tissue interface 100 on a surface wound includes placing the tissue interface 100 immediately adjacent to the surface of the body or extending over at least a portion of the surface of the body. The second layer 120 may be positioned between the first layer 110 and the third layer 130, with the third layer 130 capable of functioning, due to its lack of perforations, as an occlusive layer or drape over the first layer 110, the second layer 120, and the tissue site. The sealing strips 805 may then be placed around the perimeter of the third layer 130 of the tissue interface 100 and sealed to an attachment surface surrounding the tissue site, such as adjacent epidermis, to enable a pneumatic seal around the tissue site.

The geometry and dimensions of the tissue interface 100 may vary to suit a particular application or anatomy. For example, the geometry or dimensions of the tissue interface 100 may be adapted to provide an effective and reliable seal against challenging anatomical surfaces, such as an elbow or heel, at and around a tissue site. Thus, the tissue interface 100 can provide a sealed therapeutic environment proximate to a tissue site, substantially isolated from the external environment. In some applications, a filler may also be disposed between a tissue site and the first layer 110 of the tissue interface 100. For example, if the tissue site is a surface wound, a wound filler may be applied interior to the periwound, and the first layer 110 may be disposed over the periwound and the wound filler. In some embodiments, the filler may be a manifold, such as an open-cell foam. The filler may comprise or consist essentially of the same material as the second layer 120 in some embodiments. If not already configured, the dressing interface 830 may be disposed over an aperture formed in the third layer 130. The fluid conductor 820 may be fluidly coupled to the dressing interface 830 and to a negative-pressure source, which can reduce the pressure in the sealed therapeutic environment.

In some additional embodiments, the designs and principles of the tissue interface 100 may also be incorporated into other aspects of a dressing 800 or therapy system for treating a tissue site. For example, the laminated, layered design of the tissue interface 100 may be offered in the form of low-profile fluid conduits that may be torn and sized in a customizable fashion. Such conduits may be used in addition to or in place of a fluid conductor 820 for coupling the dressing interface 830 to a negative-pressure source. The openings 140, slits 150, and raised features 170 of the layers of the tissue interface 100 may be particularly useful for customizing the length of such a low-profile conduit, depending on the particular application to a patient. For example, some particular embodiments of the tissue interface 100 may be formed in longer strips or rolls, to allow for longer low-profile fluid conduits to be formed. Furthermore, in some embodiments, the tissue interface 100 may include specific patterns of fenestrations or other openings through the respective layers of the tissue interface 100 to facilitate custom-sizing to form a fluid conduit. For example, the tissue interface 100 may include a portion having a plurality of parallel and perpendicular rows of fenestrations, as well as an additional portion having fenestrations in a pattern of concentric circles. The portion of the tissue interface 100 having the concentric circles may be formed into an interface or landing pad where either an additional fluid conduit or possibly tissue dressing may be fluidly connected to the customized low-profile fluid conduit.

Figure 9:
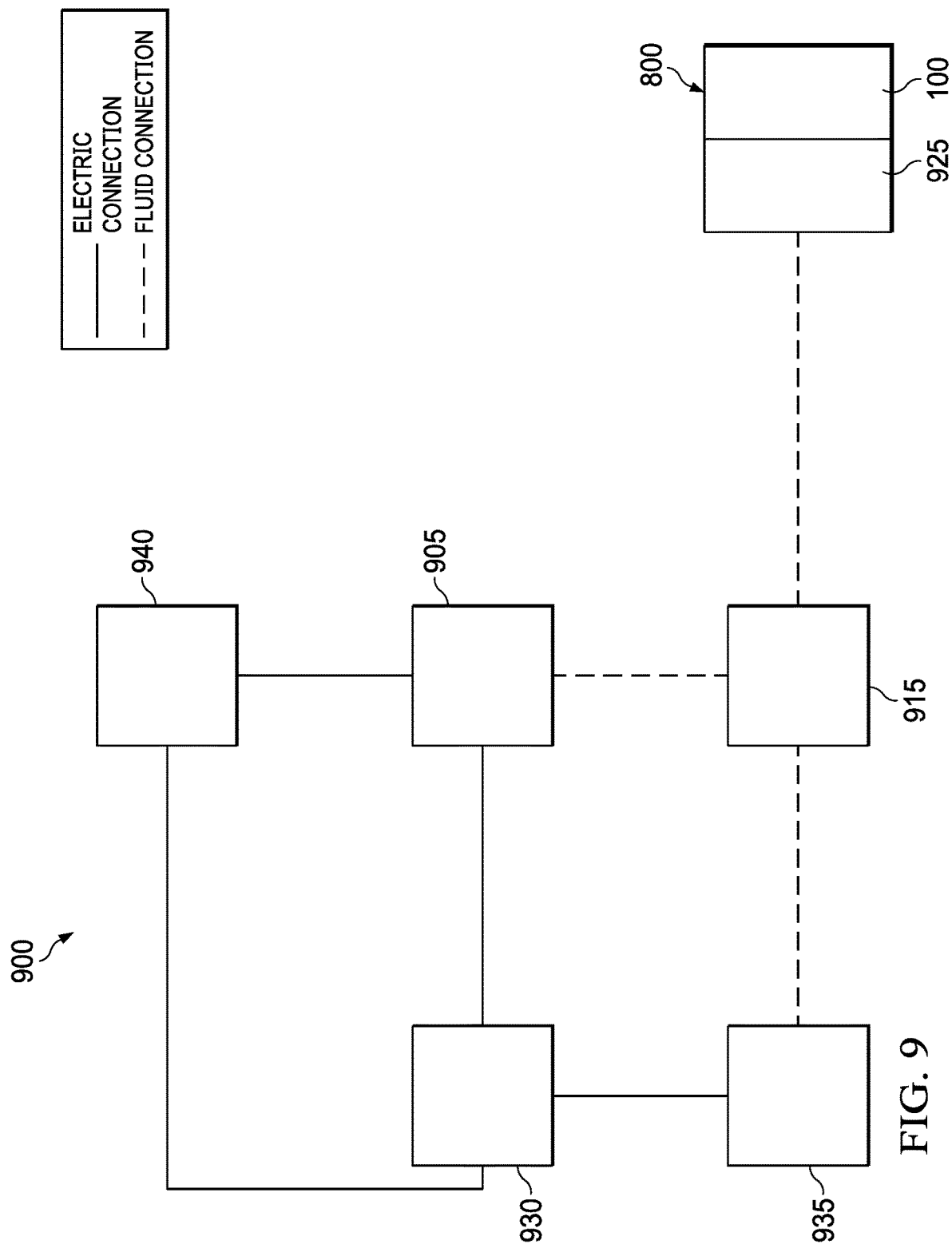
FIG. 9 is a functional block diagram of an example embodiment of a therapy system that can provide negative-pressure treatment in accordance with this specification.

FIG. 9 is a simplified functional block diagram of an example embodiment of a therapy system 900 that can provide negative-pressure therapy to a tissue site in accordance with this specification. The therapy system 900 may include a source or supply of negative pressure, such as a negative-pressure source 905, and one or more distribution components. A distribution component is preferably detachable and may be disposable, reusable, or recyclable. A dressing, such as the dressing 800, and a fluid container, such as a container 915, are examples of distribution components that may be associated with some examples of the therapy system 900. The container 915 is representative of a container, canister, pouch, or other storage component, which can be used to manage exudates and other fluids withdrawn from a tissue site. As illustrated in the example of FIG. 9, the dressing 800 may comprise or consist essentially of the tissue interface 100. In some embodiments, the dressing 800 may further include a cover 925.

In embodiments of the dressing 800 that include the cover 925, the cover 925 may provide an additional bacterial barrier and protection from physical trauma. The cover 925 may also be constructed from a material that can reduce evaporative losses and provide a fluid seal between two components or two environments, such as between a therapeutic environment and a local external environment. The cover 925 may comprise or consist of, for example, an elastomeric film or membrane that can provide a seal adequate to maintain a negative pressure at a tissue site for a given negative-pressure source. The cover 925 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties. In some embodiments, an attachment device may be used to attach the cover 925 to an attachment surface, such as undamaged epidermis, a gasket, or another cover. For example, an attachment device may be a medically-acceptable, pressure-sensitive adhesive, such as an acrylic adhesive, configured to bond the cover 925 to epidermis around a tissue site. Other examples of an attachment device may include a double-sided tape, paste, hydrocolloid, hydrogel, silicone gel, or organogel.

In some example embodiments, the cover 925 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 925 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, California; polyether block polyamide copolymer (PEBAX), for example, from Arkema S.A., Colombes, France; and Inspire 2301 and Inspire 2327 polyurethane films, commercially available from Expopack Advanced Coatings, Wrexham, United Kingdom. In some embodiments, the cover 925 may comprise INSPIRE 2301 having an MVTR (upright cup technique) of 2600 g/m$^2$/24 hours and a thickness of about 30 microns.

The therapy system 900 may also include a regulator or controller, such as a controller 930. Additionally, the therapy system 900 may include sensors to measure operating parameters and provide feedback signals to the controller 930 indicative of the operating parameters. As illustrated in FIG. 9, for example, the therapy system 900 may include a first sensor 935 and a second sensor 940 coupled to the controller 930.

Some components of the therapy system 900 may be housed within or used in conjunction with other components, such as sensors, processing units, alarm indicators, memory, databases, software, display devices, or user interfaces that further facilitate therapy. For example, in some embodiments, the negative-pressure source 905 may be combined with the controller 930 and other components into a therapy unit.

In general, components of the therapy system 900 may be coupled directly or indirectly. Coupling may include fluid, mechanical, thermal, electrical, or chemical coupling (such as a chemical bond), or some combination of coupling in some contexts.

A negative-pressure supply, such as the negative-pressure source 905, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 905 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

A controller, such as the controller 930, may be a microprocessor or computer programmed to operate one or more components of the therapy system 900, such as the negative-pressure source 905. The controller 930 may control one or more operating parameters of the therapy system 900, which may include the power applied to the negative-pressure source 905, the pressure generated by the negative-pressure source 905, or the pressure distributed to the tissue interface 100, for example. The controller 930 is also preferably configured to receive one or more input signals, such as a feedback signal, and programmed to modify one or more operating parameters based on the input signals.

Sensors, such as the first sensor 935 and the second sensor 940, are generally known in the art as any apparatus operable to detect or measure a physical phenomenon or property, and generally provide a signal indicative of the phenomenon or property that is detected or measured. For example, the first sensor 935 and the second sensor 940 may be configured to measure one or more operating parameters of the therapy system 900. In some embodiments, the first sensor 935 may be a transducer configured to measure pressure in a pneumatic pathway and convert the measurement to a signal indicative of the pressure measured. The second sensor 940 may optionally measure operating parameters of the negative-pressure source 905, such as a voltage or current, in some embodiments.

In operation, the tissue interface 100 may be placed within, over, on, or otherwise proximate to a tissue site. The cover 925 may optionally be placed over the tissue interface 100 and sealed to an attachment surface near a tissue site. For example, the cover 925 may be sealed to undamaged epidermis peripheral to a tissue site. Thus, the dressing 800 can provide a sealed therapeutic environment proximate to a tissue site, substantially isolated from the external environment, and the negative-pressure source 905 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 100 in the sealed therapeutic environment can induce macro-strain and micro-strain in the tissue site. Negative pressure can also remove exudate and other fluid from a tissue site, which can be collected in container 915. For example, negative pressure applied through the tissue interface 100 can create a negative pressure differential across the openings 140 in the first layer 110, which can open or expand the openings 140 from their resting state. For example, in some embodiments in which the openings 140 may comprise substantially closed fenestrations through the first layer 110, a pressure gradient across the fenestrations can strain the adjacent material of the first layer 110 and increase the dimensions of the fenestrations to allow liquid movement through them, similar to the operation of a duckbill valve. Opening the openings 140 can allow exudate and other liquid movement through the openings 140, through the second layer 120, the third layer 130, and into the container 915. Changes in pressure can also cause the second layer 120 to expand and contract, and the first layer 110 may protect the epidermis from irritation caused by the movement of the second layer 120. The first layer 110 can also substantially reduce or prevent exposure of tissue to the second layer 120, which can inhibit growth of tissue into the second layer 120.

In some embodiments, the controller 930 may receive and process data from one or more sensors, such as the first sensor 935. The controller 930 may also control the operation of one or more components of the therapy system 900 to manage the pressure delivered to the tissue interface 100. In some embodiments, controller 930 may include an input for receiving a desired target pressure and may be programmed for processing data relating to the setting and inputting of the target pressure to be applied to the tissue interface 100. In some example embodiments, the target pressure may be a fixed pressure value set by an operator as the target negative pressure desired for therapy at a tissue site and then provided as input to the controller 930. The target pressure may vary from tissue site to tissue site based on the type of tissue forming a tissue site, the type of injury or wound (if any), the medical condition of the patient, and the preference of the attending physician. After selecting a desired target pressure, the controller 930 can operate the negative-pressure source 905 in one or more control modes based on the target pressure and may receive feedback from one or more sensors to maintain the target pressure at the tissue interface 100.

If the negative-pressure source 905 is removed or turned-off, the pressure differential across the openings 140 of the first layer 110 of the tissue interface 100 can dissipate, allowing the openings 140 to move to their resting state and prevent or reduce the rate at which exudate or other liquid can return to the tissue site through the first layer 110.

The systems, apparatuses, and methods described herein may provide significant advantages. For example, some dressings and tissue interfaces for applying to tissue sites can require time and skill to be properly sized and applied to achieve a good fit and seal, in addition to requiring one or more cutting or sizing tools. In contrast, some embodiments of the tissue interface 100 may be applied to a tissue site with simple sizing and cutting steps, therefore reducing the amount of time and effort as compared to some previous dressings. For example, the tissue interface 100 may be torn by hand, without requiring the use of scissors or scalpels. Importantly, multiple layers of the tissue interface 100 may be torn at once, thus obviating challenges associated with separately sizing the individual layers and potential sizing inconsistencies between the layers. Thus, the tissue interface 100 may offer a fully-integrated dressing that can be easily cut and applied to a tissue site (including over the peri-wound), while providing many benefits of other dressings that may require more complex sizing protocols. Such benefits may include good manifolding, beneficial granulation, and protection of the peripheral tissue from maceration. The tissue interface 100 may also conform to and occupy a significant space at a tissue site, which may be particularly advantageous for wounds having moderate depth and medium-to-high levels of exudate. Additionally, the tissue interface 100 can promote granulation while reducing the opportunity for tissue in-growth by containing the porous foam material within other film layers. As a result, the tissue interface 100 can be worn for extended wear times, for example up to seven days.

The designs of some embodiments of the tissue interface 100 may also allow for a more custom- or specifically-tailored size of the tissue interface 100 to be accomplished, as compared to some other dressing materials commercially available, such as dressing materials which may include only large, pre-cut sections. For example, the plurality of the openings 140 of the first layer 110, the slits 150 of the second layer 120, and the raised features 170 of the third layer 130 may allow for one or more tear lines to be made through the tissue interface 100 at specific locations, thus allowing the size of the tissue interface 100 to closely correspond to the area or size of the tissue site to which it is to be applied. The flexibility offered by being able to tear the tissue interface 100 along multiple specific lines may also result in fewer wasted dressing materials. For example, a user may make multiple or repeated tears through the tissue interface 100 in order to make adjustments to the size of the tissue interface 100 to accomplish an appropriate fit for the tissue site being treated.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the tissue interface 110, the container 915, or any other disclosed components may be separated from other components for manufacture or sale. In other example configurations, the controller 930 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing material, comprising:
 a first layer comprising a first film of non-porous material having a plurality of openings;
 a second layer adjacent to the first layer, the second layer comprising a manifold having a plurality of slits; and
 a third layer adjacent to the second layer and comprising a second film of non-porous material having raised features, wherein the second layer is positioned between the first layer and the third layer;
 wherein at least some of the plurality of openings, some of the plurality of slits, and some of the raised features are aligned to define a tear line, and wherein the raised features are overlaid upon the plurality of openings and the plurality of slits such that the raised features are configured to be torn along the tear line.

2. The dressing material of claim 1, wherein the first film comprises a polyurethane material.

3. The dressing material of claim 1, wherein the manifold comprises a porous foam including a plurality of interconnected fluid pathways defined by pores in the porous foam in addition to the plurality of slits, and wherein the plurality of slits comprise linear fenestrations disposed through a thickness of the porous foam.

4. The dressing material of claim 1, wherein:
 the first film comprises a polyurethane material; and
 the second film comprises a polyurethane material.

5. The dressing material of claim 1, wherein:
 the plurality of openings and the plurality of slits are configured as pairs of aligned openings and slits.

6. The dressing material of claim 1, wherein the first film is an adhesive-coated film.

7. The dressing material of claim 1, wherein:
 the plurality of openings are distributed across the first layer in parallel rows and columns; and
 the rows are spaced about 3 mm on center.

8. The dressing material of claim 1, wherein:
 the plurality of openings are distributed across the first layer in parallel rows and columns;
 the rows are spaced 3 mm on center; and
 the openings in each of the rows are spaced about 3 mm on center.

9. The dressing material of claim 8, wherein the plurality of openings in adjacent rows are offset.

10. The dressing material of claim 1, wherein:
 the second film is an adhesive-coated film; and
 the second film is laminated to the second layer.

11. The dressing material of claim 1, wherein the second film is a highly-breathable film.

12. The dressing material of claim 1, wherein at least some of the plurality of openings, some of the plurality of slits, and some of the raised features are aligned in a linear pattern.

13. The dressing material of claim 1, wherein at least some of the plurality of openings, some of the plurality of slits, and some of the raised features are aligned in a pattern having geometric shapes.

14. The dressing material of claim 13, wherein the geometric shapes comprise one or more squares or circles.

15. A system for treating a tissue site, comprising:
 a wound filler, comprising:
  a first layer comprising a first film of non-porous material,
  a second layer adjacent to the first layer, the second layer comprising porous foam,
  a third layer adjacent to the second layer and comprising a second film of non-porous material having raised features, wherein the second layer is positioned between the first layer and the third layer, and
  a plurality of fenestrations extending through the first layer and the second layer, wherein the plurality of fenestrations through the first layer are aligned with the plurality of fenestrations through the second layer, and wherein the raised features of the third layer are overlaid upon the plurality of fenestrations through the first layer and the second layer such that the raised features are configured to be torn along a tear line defined by the plurality of fenestrations;
 a plurality of sealing strips adapted to be positioned over a perimeter of the third layer opposite the second layer; and
 an interface adapted to be coupled to the wound filler.

16. The system of claim 15, further comprising a negative-pressure source adapted to be fluidly connected to the wound filler through the interface.

17. The system of claim 15, wherein:
 the first film comprises a polyurethane material; and
 the foam comprises a polyurethane foam.

18. The system of claim 15, wherein each of the plurality of fenestrations is linear and has a length between 1 mm and 5 mm.

* * * * *